United States Patent [19]

Bennett

[11] Patent Number: 5,602,180

[45] Date of Patent: Feb. 11, 1997

[54] METHOD OF ADMINISTERING EDTA COMPLEXES

[75] Inventor: Ronald Bennett, Laughlin, Nev.

[73] Assignee: World Health Group, Laughlin, Nev.

[21] Appl. No.: 416,038

[22] Filed: Mar. 31, 1995

[51] Int. Cl.$^6$ .............................. A01N 37/00; A01J 25/12
[52] U.S. Cl. ...................... 514/578; 514/964; 424/457; 424/DIG. 15
[58] Field of Search ..................................... 514/578, 667, 514/964; 424/DIG. 15, 457; 562/566

[56] References Cited

U.S. PATENT DOCUMENTS

| | | | |
|---|---|---|---|
| 4,107,331 | 8/1978 | Rosenberg | 424/319 |
| 5,208,324 | 5/1993 | Klaveness et al. | 534/16 |
| 5,281,704 | 1/1994 | Love et al. | 540/465 |

*Primary Examiner*—Nathan M. Nutter
*Attorney, Agent, or Firm*—Shoemaker and Mattare, Ltd.

[57] ABSTRACT

A method of administering EDTA complexes includes steps of forming a suppository containing an EDTA complex and controlled-release agents which release the EDTA complex over a period of about three to four hours after placement, and then administering the suppository to a patient in lieu of an intravenous drip.

2 Claims, No Drawings

METHOD OF ADMINISTERING EDTA COMPLEXES

BACKGROUND OF THE INVENTION

This invention relates to the art of medicine and more particularly to a method of administering EDTA complexes.

Chelation therapy, involving the administration of EDTA (ethylene diamine tetraacetic acid) complexes, for removing arterial calcium plaque, or for removing heavy metals such as lead and mercury, has been practiced for many years. It is normally administered intravenously to a patient, who must remain relatively immobile for about three and a half to four hours each session. The normal schedule is three sessions a week for three months. Such frequent immobilization inconveniences the patient, and requires considerable dedicated floor space at the administration facility. An alternative method of administration would be preferred by many doctors and patients.

Oral ingestion of EDTA is impractical, inasmuch as stomach acids destroy its effectiveness.

I have discovered that EDTA can be administered in other ways, especially rectally, in suppository form, provided that the EDTA is bound in a container, matrix or vehicle which releases it slowly, over a period of hours.

Prior inventors have developed suppositories with time-release capability for other medications. The materials employed vary. Usually, the bulk of the suppository is an inert waxy carrier in which the medication is dissolved or suspended. Early suppositories used a material, such as gelatin, which dissolved slowly in the intestine. More recently, synthetic polymers have been used, as have metal salts in a matrix which regulates the release of medication. Representative prior U.S. patents include U.S. Pat. Nos. 4,265,875; 4,292,300; 4,406,883; 5,151,434; 5,188,840; 5,215,758; 5,352,455 and 5,393,528. All the patents identified in the preceding sentence are hereby incorporated in this specfication by reference.

SUMMARY OF THE INVENTION

An object of the invention is to reduce the amount of time that a patient must remain in a physician's office to receive chelation therapy.

Another object of the invention is to make it possible for a patient to administer EDTA complexes to himself at any convenient time, such as before retiring.

A further object of the invention is to increase the efficiency of chelation therapy practice.

These and other objects are attained by a method of administering EDTA complexes comprising steps of forming a suppository containing EDTA complexes and controlled-release agents which release the EDTA complexes over a period of about three to four hours after placement, and then administering the suppository to a patient in lieu of an intravenous drip.

Alternatively, the invention can be practiced transdermally, for example in patch form.

It is expected that either dosage form will greatly reduce the number of office visits for patients, who may need to visit a facility only once a month for blood and urine chemistry and perhaps thermography or Doppler tests to evaluate vessel occlusion. I anticipate also that daily dosages can be reduced from their current level, as it will be convenient to extend the treatment session duration from three to six months.

DESCRIPTION OF THE PREFERRED EMBODIMENT

A therpeutic method according to the invention comprises steps of forming an EDTA complex containing suppository with a controlled release matrix. The presently preferred complex is disodium EDTA. The suppository is molded, in a common shape, from a waxy material in which the active ingredients have been dissolved or suspended. The base material may comprise glycerin, glyceryl monopalmitate, glyceryl monostearate, hydrogenated coconut oil fatty acids and hydrogenated palm kernel oil fatty acids. The choice of base materials is a matter of ordinary skill.

Methods of making controlled-release suppositories are well known. Choosing suitable carrier materials, and suitable matrix ingredients, are within the skill of the artisan in this field, making reference to the patents mentioned above, and others. The release-controlling agents, and their concentrations, should be chosen so that release occurs within the body over a three to four hour period after the suppository is administered.

Since the invention is subject to modifications and variations, it is intended that the foregoing description and the accompanying drawings shall be interpreted as only illustrative of the invention defined by the following claims.

I claim:

1. A method of administering EDTA complexes to a patient, said method comprising steps of forming a suppository containing disodium EDTA and controlled-release agents which release the disodium EDTA over a period of about three to four hours after placement in the anus, and then administering the suppository to the patient.

2. A suppository for chelation therapy, said suppository comprising an inert meltable carrier containing dissolved or suspended disodium EDTA and a controlled-release matrix for releasing the complexes into the body over a period of three to four hours after anal administration of the suppository.

* * * * *